(12) United States Patent
Cezar

(10) Patent No.: US 6,517,817 B1
(45) Date of Patent: Feb. 11, 2003

(54) FOOT SOFTENING COMPOSITION AND PROCESS FOR MAKING SAME

(76) Inventor: John Cezar, 4745 Park, Apt#2, Beaumont, TX (US) 77705

( * ) Notice: Subject to any disclaimer, the term of this patent is extended or adjusted under 35 U.S.C. 154(b) by 0 days.

(21) Appl. No.: 10/061,743

(22) Filed: Feb. 4, 2002

(51) Int. Cl.[7] .............................. A61K 7/04; A61K 6/00; A61K 7/00; A61K 9/14
(52) U.S. Cl. ........................ 424/61; 424/401; 424/489
(58) Field of Search ................................ 424/489, 401, 424/61

(56) References Cited

U.S. PATENT DOCUMENTS

| | | | | |
|---|---|---|---|---|
| 4,550,035 A | * | 10/1985 | Smith ...................... | 427/398.1 |
| 4,569,839 A | * | 2/1986 | Grollier et al. ............... | 424/74 |
| 4,963,591 A | * | 10/1990 | Fourman et al. ............. | 514/944 |
| 5,631,012 A | * | 5/1997 | Shanni ........................ | 424/401 |
| 5,744,062 A | * | 4/1998 | Dahms et al. ............... | 252/312 |
| 6,342,208 B1 | * | 1/2002 | Hyldgaard et al. ........... | 424/59 |

* cited by examiner

Primary Examiner—Thurman K. Page
Assistant Examiner—Simon J. Oh
(74) Attorney, Agent, or Firm—Kenneth D. Baugh

(57) ABSTRACT

The foot composition of this invention contains a mixture of lamb fat, water, peppermint oil and mineral oil. The foot composition is provided to soften and cure dry feet as well as remove calluses and corns.

11 Claims, No Drawings

FOOT SOFTENING COMPOSITION AND PROCESS FOR MAKING SAME

This invention relates to foot compositions and more particularly to a foot composition for use in softening and curing dry feet as well as removing calluses and corns. In our fast pace society individuals often find it difficult to properly care for their feet. AS a result, individuals often experience the more common conditions such as harden dry feet, with calluses and corns. One of the common ways to address these conditions is by availing ones self of the foot treatment processes that are made available at commercial establishments which are designed specifically for that purpose. Obviously this is not always the most desirable alternative because in order to achieve the result they provide you must leave the comfort of your home. The most desirable way to address these foot problems is with a composition that can be used at home. However, none of the commercially available compositions can be used in softening and curing dry feet as well as removing calluses and corns. Accordingly there becomes a need to provide an ointment to address these feet conditions without having to leave your home. Specifically a composition that can be used in the comfort of your home which can be used in softening and curing dry feet and removing calluses and corns is desired.

BACKGROUND ARTS

Attempts have been made to provide a composition for treating the various conditions of the feet. One such composition is disclosed in U.S. Pat. No. 5,702,694. This composition relates to a topical composition for treating corns, calluses and warts which comprises a benzenediol. Included among benzenediols are benzenediols or substituted benzenediols selected from the group consisting of hydroguinone, olivetol, pyrocatechol 2,5-dihydroxy benzoic acid; or 1,2-benzenediols substituted in 4-position selected from the group consisting of nordihydrogualaretic acid (NDGA) and 4-nitrocatechol in combination with a pharmaceutically acceptable carrier. Another composition is disclosed in U.S. Pat. No. 5,686,083. In this product a topical composition for treating corns and calluses is provided which consists of 4 carbon $\alpha$-keto acid, most preferably $\alpha$-ketebulric acid, or its corresponding salts or esters in combination with a pharmaceutically acceptable carrier.

Although both these products achieve the desired results both the products disclosed in these patents are designed specifically for the treatment of corns and calluses on the feet. They are not also designed for softening and curing dry feet. Additionally, because of the unique ingredients required these products may be expensive and somewhat difficult to make. Accordingly it is desirable to provide a product which also softens and cures dry feet while also treating corns and calluses which can be made from readily available ingredients, which is easy to prepare and has the unique results and advantages of the present invention.

DISCLOSURE OF THE INVENTION

The invention relates to an Improved foot soften composition. The composition in accordance with the principles of the invention is provided in predetermined weight quantities with a mixture of lamb fat, peppermint essential oil, mineral oil and water.

DETAIL DESCRIPTION OF THE INVENTION

In accordance with the preferred embodiment of the invention a novel composition is provided. The composition in accordance with the present invention contains on a weight basis 76% lambs fat, 0.3% peppermint essential oil, 4.7% mineral oil, and 19% water.

A typical process for preparation of the foot composition includes a first step of mixing the lambs fat and water together at ambient temperature. Once these ingredients are mixed together they are cooked over a high temperature between 220° F. and 250° F. for approximately ninety to one hundred twenty minutes or until the solid fat particles or residue in the lamb's fat is separated from oil and rises to the top of the solution therein thereby forming a first homogenous mixture of oil. The first homogenous mixture of oil is then sifted so that the residue is removed. This first mixture is then cooled to approximately 80% of the cooking temperature that is between 176° F. and 200° F. Once the mixture is cooled the remaining ingredients, that is, the peppermint oil and mineral oil are mixed with the first homogenous mixture of oil for a minute thereby forming a second homogenous mixture. Then the second homogenous mixture is cooled to ambient temperature thereby forming a solid paste-like substance. The resulting paste-like substance is the foot soften composition of this invention.

The foot softening ointment is then packaged in containers as desired.

When one is in need of softening one's feet or removing the corns or calluses thereon, the composition can be maintained in the solid paste-like state or heated until it returns to a liquid state. The composition of this invention is then applied to the feet in the affected areas. The composition is then maintained thereon for approximately eight hours as the user goes about their normal activities. The composition can be properly maintained on the feet during this period by wearing thick socks over the feet such as, for example, those socks known as tube socks.

The invention has been shown and described in what is considered to be the most practical and preferred embodiments. However, it should be recognized that changes may be made by those skilled in the art without departing from the spirit and scope of the invention.

What is claimed is:

1. A process for making a foot composition consisting of:
   blending together composition ingredients including by weight 76% lambs fat and 19% water at a first predetermined temperature;
   cooking these ingredients at a second predetermined temperature for a first predetermined time so that a first homogenous mixture is formed with a residue at the upper portion thereof;
   sifting the first homogenous mixture so that the residue is removed;
   allowing the first homogenous mixture to cool for a second predetermined time to reach a third predetermined temperature;
   mixing the remaining ingredients of 0.3% peppermint essential oil and 4.7% mineral oil, together with the first homogenous mixture to form a second homogenous mixture;

allowing the second homogenous mixture to cool to the first predetermined temperature so that a solid a pasty substance forms; and packaging the mixture in a container.

2. A process as defined in claim 1 wherein the first predetermined temperature is ambient temperature.

3. A process as defined in claim 2 wherein the second predetermined temperature is between 220° F. and 250° F.

4. A process as defined in claim 3 wherein the third predetermined temperature is between 176° F. and 200° F.

5. A process as defined in claim 4 wherein the first predetermined time is between ninety and one hundred twenty minutes.

6. A process as defined in claim 5 wherein the second predetermined time is one minute.

7. A foot composition product made by the process of claim 1.

8. A foot composition product made by the process of claim 2.

9. A foot composition product made by the process of claim 3.

10. A foot composition product made by the process of claim 4.

11. A foot composition product made by the process of claim 5.

\* \* \* \* \*